US010776455B2

(12) United States Patent
Reddy et al.

(10) Patent No.: US 10,776,455 B2
(45) Date of Patent: Sep. 15, 2020

(54) METHOD AND SYSTEM FOR MANAGING THE USE OF DIETARY SUPPLEMENTS AND DRUGS THROUGH MOBILE DEVICES

(71) Applicant: SEROTONIN, INC., San Francisco, CA (US)

(72) Inventors: Rajesh Reddy, Burlingame, CA (US); Amoghavarsha Janakaloti Shamarao, Bangalore (IN)

(73) Assignee: Serotonin, Inc., Burlingame, CA (US)

( * ) Notice: Subject to any disclaimer, the term of this patent is extended or adjusted under 35 U.S.C. 154(b) by 1384 days.

(21) Appl. No.: 14/873,209

(22) Filed: Oct. 2, 2015

(65) Prior Publication Data

US 2017/0098056 A1  Apr. 6, 2017

(51) Int. Cl.
*G06F 19/00* (2018.01)

(52) U.S. Cl.
CPC .................. *G06F 19/3456* (2013.01)

(58) Field of Classification Search
CPC ............ G06F 19/3475; G06F 19/3418; G06F 19/3456; G06Q 50/22; G06Q 10/10; G16H 10/60; G16H 20/60; G16H 50/20
USPC ............................................................ 705/4
See application file for complete search history.

(56) References Cited

U.S. PATENT DOCUMENTS

| 7,295,889 B2 | 11/2007 | Lähteenmäki |
| 2003/0010791 A1 | 1/2003 | Gentiluomo |
| 2003/0069757 A1 | 4/2003 | Greenberg |
| 2006/0136266 A1 * | 6/2006 | Tarassenko ............ G06Q 50/24 705/3 |
| 2007/0093935 A1 * | 4/2007 | Fu ........................ G06F 19/3456 700/237 |
| 2007/0185615 A1 * | 8/2007 | Bossi .................. G07F 17/0092 700/244 |
| 2009/0134181 A1 * | 5/2009 | Wachman .............. G06Q 10/10 221/8 |

(Continued)

FOREIGN PATENT DOCUMENTS

CA  2587240 A1  5/2006

OTHER PUBLICATIONS

"ADHD Medication Titration Process: What to Expect" http://www.webmd.com/add-adhd/guide/adhd-medication-titration Reviewed by Smitha Bhandari, MD Jun. 4, 2015.

(Continued)

*Primary Examiner* — Joy Chng
(74) *Attorney, Agent, or Firm* — Run8 Patent Group, LLC; Peter Miller

(57) ABSTRACT

A mobile apparatus for monitoring and managing periodic intake of dietary supplements or drug-based products utilizing user health and wellbeing updates. The mobile apparatus is a mobile computing device configured to execute a mobile application. The mobile application accepts periodic health and wellbeing information from a user and other connected monitoring devices, accepts user goal updates, accepts effectiveness feedback from the user, displays messages recommending dietary supplement and drug dosages and dosage schedules to the user, notifies the user when to take the dosage, accepts messages detailing the dosage intake and updates the estimated amount of material available, sends messages to re-order material, and provides feedback to the user based on measurement of actual usage.

20 Claims, 16 Drawing Sheets

(56) References Cited

U.S. PATENT DOCUMENTS

| | | |
|---|---|---|
| 2010/0266723 A1 | 10/2010 | Bralley et al. |
| 2011/0014351 A1 | 1/2011 | Reider |
| 2012/0083669 A1* | 4/2012 | Abujbara ............ G06F 19/3475 600/300 |
| 2013/0022951 A1 | 1/2013 | Hughes |

OTHER PUBLICATIONS

Niacin: Myths and Facts Dr. William Davis Dec. 17, 2007 http://www.healthcentral.com/cholesterol/c/7986/17940/myths-facts/.

* cited by examiner

METHOD AND SYSTEM FOR MANAGING THE USE OF DIETARY SUPPLEMENTS AND DRUGS THROUGH MOBILE DEVICES

FIELD OF THE INVENTION

This invention generally relates to the management of health and wellness through the automated management of the intake of dietary supplements and drugs.

BACKGROUND AND DESCRIPTION OF THE RELATED ART

People try to manage health and wellness through a combination of a balanced diet and exercise. Dietary supplements are necessary for a healthy body and mind because of the gaps that occur based on normal variations in diet and schedules. In other cases, drugs are needed to keep the body healthy and fight diseases.

Today the market is filled with dietary supplements and drugs. However, the benefits drawn from these are not optimum. One reasons is that the substances are generic and not customized for an individual. Dietary supplements and drugs are marketed using a pre-packaged, one-size-fits-all approach. Although there are some variations, it is mostly the same irrespective of lifestyle, age, body/mind conditions and changing individual requirements.

The benefits of these substances decrease if they are not taken on a schedule. The body will utilize or remove nutrients over time, and so the desired effects may not be achieved if the substances are taken randomly or sporadically.

Furthermore, individual requirements change over time. For example, a person who has completed a long exercise regimen or is in bed with the flu has different requirements. Knowing the current state of the user and their usage is needed to fine tune the substance mix and dosage periodically.

One aspect to dose management is medication titration. In medicine, titration is the process of gradually adjusting the dose of a medication until optimal results are reached. For an example of this, see "ADHD Medication Titration Process: What to Expect" at http://www.webmd.com/add-adhd/guide/adhd-medication-titration. The same thing is true for dietary supplements.

In 2002, Sanford Greenberg described a system that would provide a nutritional supplement regime based on a questionnaire that would ask questions on nutritional habits, exercise habits, health information and personal goals of the individual (US 20030069757 Ser. No. 10/265,537 2002). On completing the questionnaire, the user would receive the supplements in a case. No means to monitor the effects once the user receives the supplements or modify the dosages is provided by this system.

In 2002, Gentiluomo et al described a system that would dispense a customized pharmaceutical mixture from a plurality of containers containing multiple pharmaceutical substances based on the particular health information provided by a user and remind the user to take it (US20030010791 Ser. No. 10/194,001 2002). Once the user enters health information, there is no means to monitor its effects on the user or to modify the dosages based on the user's use or perceived effects of the mixture by the user.

In 2002, Pertti Lähteenmäki described a nutrition dispenser that would dispense doses of nutrients and/or medications from rooms based on the user's genetic background and inputs from the user and one or more probability weighting coefficients between various parameters (U.S. Pat. No. 7,295,889 2002). This dispenser dispenses nutrients based on an analysis of the user's needs based on a single set of calculations, with no system for monitoring the actual dosages or effects over time.

In 2005, Ralph Koekkoek described a system that would compound a personalized nutritional supplement based on genotypic analysis, phenotypic analysis, a list of one or more nutritional needs and a nutritional supplement recipe (CA 2587240 2005). The resulting compound is presented to the user, and if needs change or if the desired effect is not achieved there is no mechanism presented.

In 2005, Bralley et al described a system that would prepare a metabolic supplement from micronutrients based on a metabolic profile from a specimen from a subject (US20100266723 Ser. No. 12/451,623). The resulting compound is based on no input from the user and there is no mechanism presented to monitor the usage or effects over time.

In 2010, Reider et al described a system that would provide a recommended daily supplement package based on a single requested user questionnaire (US 20110014351 Ser. No. 12/837,210 2010). On completing the questionnaire, the user would receive a list of supplements. In this system, there is no dispensing, ordering, or feedback mechanism presented.

In 2011, Nabil M. Abujbara described a system that would accept health information and personal attributes of a user, presenting the user with a food item list and continuously updating the list based on entry of the actual food items consumed and changes in the user's reported health and food consumption information. (US 20120083669 Ser. No. 13/252,620). The system requires the user to manage the supplement intake without the benefit of a dispensing mechanism to prepare the supplements, to re-order the supplements when it is detected they are running out, or to monitor the actual usage of supplements.

In 2011, Timothy Hughes described a method of providing a four-week container and supplement dispenser with intra-daily compartments, the contents of which are based on genetic analysis (US 20130022951 Ser. No. 13/136,041). In this system, there is no dispensing mechanism to monitor the actual usage, nor is there any mechanism presented to change the supplement makeup as the contents are based on a fixed mechanism (genetic analysis).

What is needed is mobile apparatus to monitor the intake of dietary supplements and drugs that can continuously fine tune the mix and dosage of the substances, adapting to the changes in the personal goals and health of a user and the user's consumption of and reaction to the substances, and further improve adherence to the program by providing feedback and encouragement to the user based on their actual usage.

OVERVIEW

Summary

A mobile apparatus for monitoring and managing of periodic intake of dietary supplements and drugs utilizing user health and wellbeing updates. The mobile apparatus is a mobile computing device configured to execute a mobile application. The mobile application accepts periodic health and wellbeing information from a user and other connected monitoring devices, accepts user goal updates, accepts effectiveness feedback from the user, makes recommendations for changes in dosage based on information provided by the user as well as aggregated data from other users, displays messages recommending dietary supplement and drug dosages and dosage schedules to the user, notifies the user when to take the dosage, accepts messages detailing the dose intake and updates the estimated amount of dietary supplement and drug material available, sends messages to re-order materials, and provides feedback to the user based on measurement of actual usage.

BRIEF DESCRIPTION OF THE DRAWINGS

A better understanding of the present invention can be obtained from the following detailed description in conjunction with the following drawings, in which.

DETAILED DESCRIPTION

Systems have been implemented over the years to dispense nutrients to users. Some of these systems dispense a fixed amount of dietary supplements or drugs (a dosage) based on an analysis of the user's health and goals, but there is no feedback as the person's health or goals change. Even where there is tracking, it is either too vague or too infrequent. For the dietary substances or drugs to be effective, they must be administered over a period of time. Over that period of time, users need to adhere to the plan and the plan needs to change with the user's needs. This requires a process for reminders, a process for automated tracking of the user's usage of the nutrients, a process to accurately measure the impact on the user over time and to leverage that information to provide a customized program for that specific user, and a process for encouragement of the user to enable the user to build a habit.

Managing the dosage of dietary supplements and drugs requires continuous interaction with the user that with current technology, requires that one leverage mobile technology to do so. The invention enables the continuous monitoring of the user while interacting with the means of dispensing and order substance is described herein.

By "dietary supplements and drugs", we are referring to those substances which are taken with the goal of improving one's health and wellbeing. These include but are not limited to pharmaceutical drugs, minerals, vitamins, and herbal mixtures.

The dosage may include one or more independent dietary supplement or pharmaceutical products. The mobile apparatus includes the functionality to order one or more of these products, and monitor the level of each product based on received messages that detail the amount of each product when the order is received by a user, or based on received messages detailing the amount of each product in a dosage taken by a user.

Figure 1:
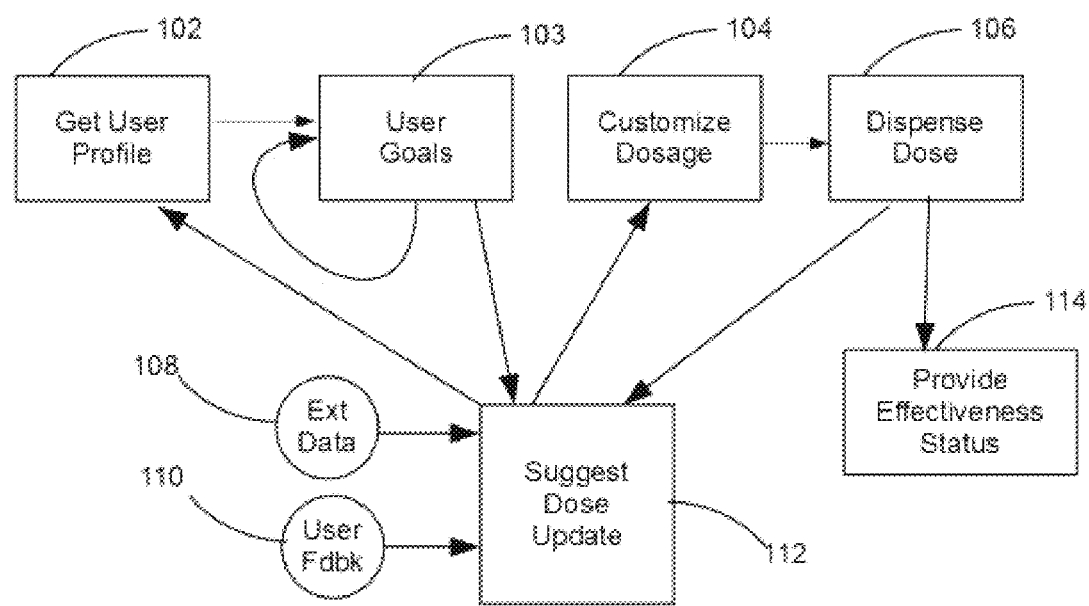
FIG. 1 shows an embodiment of the system flow associated with the mobile apparatus.

FIG. 1 shows an embodiment of the mobile apparatus. After getting the user profile data 102 and accepting user goals 103, a dosage consisting of a mixture of one or more dietary supplements or drugs can be suggested 112, and the dosage can be customized 104 based on user input. The apparatus accepts a notification message that the user has taken the dosage 106 and adherence to the plan is monitored, providing encouragement to enforce the habit 114. Over time, the user's adherence, periodic user input 110, and health and wellbeing data from a variety of sources 108 are input to the system to provide feedback in order to customize the supplement dosage over time 104. Further, the user may choose to update personal goals as the situation changes 103, and a new dosage may be recommended as a result 112.

Figure 2:
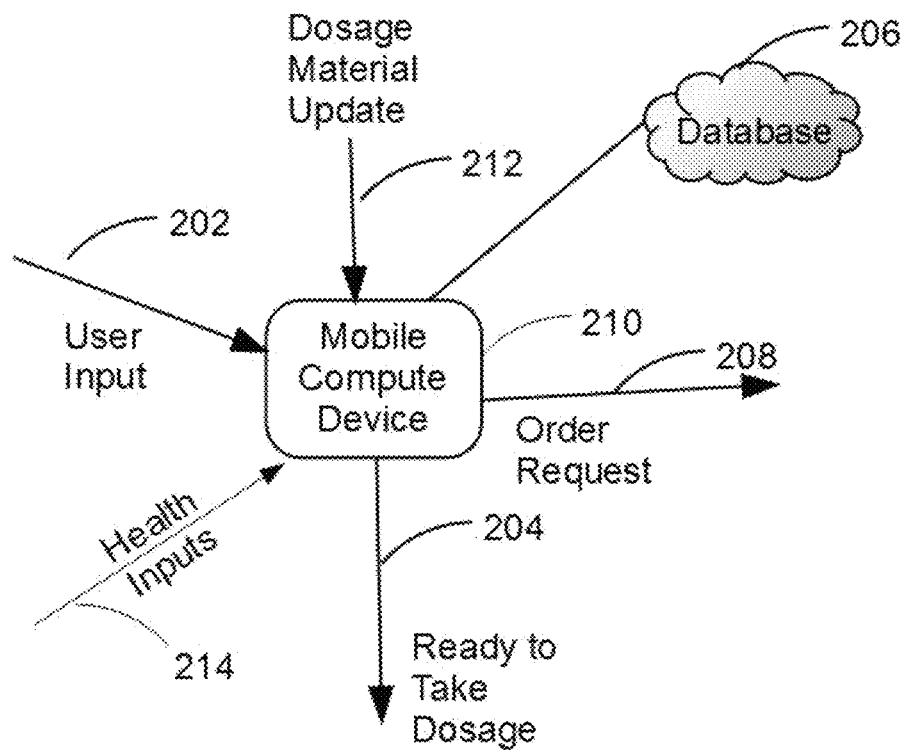
FIG. 2 shows an embodiment of the operating environment of the apparatus.

FIG. 2 depicts an embodiment of the operating environment of the mobile apparatus. A mobile compute device 210 accepts subscription and health information from a user. The responses are stored in a database 206 where the entries are associate the user with that subscription and health information. The database also stores user feedback, aggregated user data, the amount of each product available, dispensed and dosage history. In one or more embodiments the database is configured to accept aggregated user data from other users.

In one or more embodiments, the mobile compute device 210 sends a message to order one or more dietary supplement or drug products 208. In one or more embodiments, this would include the health information. In one or more embodiments, the mobile compute device 210 is configured to accept details of each dosage in terms of how much of each drug or dietary supplement product is required for each dose 212. In one or more embodiments, the mobile compute device 212 is configured to remind the user when it is time to take a dose, to provide messages to a user to encourage them, and customizing the encouragement messages based on the user's adherence to the plan.

In one or more embodiments, the mobile compute device 210 would be a mobile device such as a smart phone or tablet. As such, software configured to run on the mobile compute device 210 would have access to the devices that are embedded in the smart phone or tablet such as clocks, motion sensors, accelerometers, GPS and gyroscopes. The software configured to run on the mobile compute device 210 would also have access to devices that are in proximity to the mobile device and can communicate with the mobile device such as a smart wrist band, which could allow the collection of fitness data, blood oxygen levels, heart rate or respiration rate.

When a user is ready to take a dosage, a message is sent requesting a dose 204. The mobile compute device 210 is also configured to accept a notification of how much of each dietary supplement or drug-based product was taken 212. Modules in the mobile compute device 210 can then calculate when one or more of the products will run out, and send out a message 208 to order the required products with enough advance notice to assure that the user will have the products available. In one or more embodiments, the mobile compute device will be configured to be account for the estimated delivery time for the materials when it predicts when a new order should arrive. The mobile compute device is also configured to accept a message 212 when dietary supplement and drug products are received.

Figure 10:
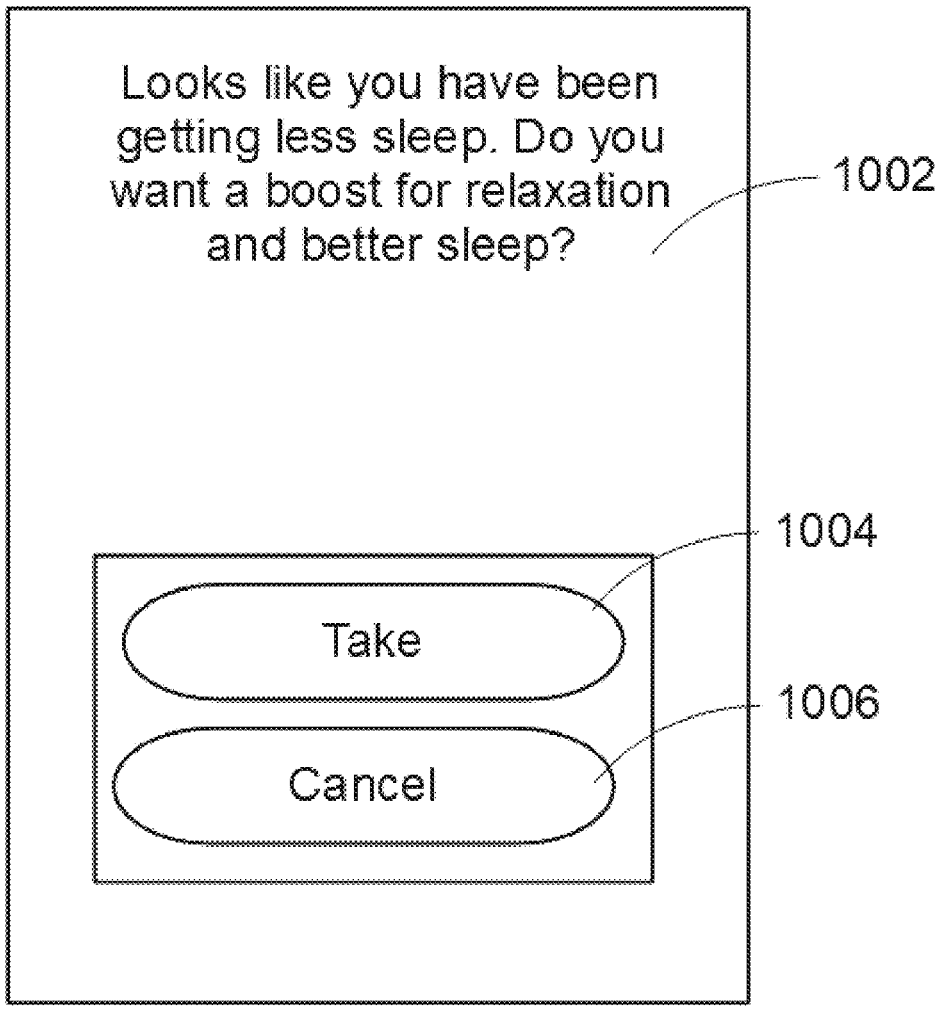
FIG. 10 shows one or more embodiments of a display to recommend an off-schedule dosage to a user.

In one or more embodiments, a software module in the mobile compute device 210 can be configured as a Recommendation Engine 314. The Recommendation Engine 314 is configured to make recommendations to modify a person's dosage as a mixture of one or more drug and dietary supplements based on user profile, user feedback, personal goals, health history, individual user dosage history, and aggregated information from other users with a similar profile. In one embodiment, the Recommendation Engine 314 determines that a user has been awake much longer than he/she is normally and recommends a supplement boost, as shown in FIG. 10. A boost is an off-schedule dosage, which is recommended to be dispensed to the user based on exigent circumstances (too little sleep, changing time zones, a user request). In one or more embodiments, a user interface displays a message to the user recommending a supplemental dosage to help them sleep better 1002. The user is then given the option to take 1004 or cancel 1006 the dispensing of the supplemental dosage. If the user selects take 1004, a message is sent requesting to the supplemental dosage 204. The Dispenser Manager 304 is configured to accept a message confirming that the supplemental dosage was taken 212.

In one or more embodiments, a knowledge base configured in the database 206 that is used by the Recommendation Engine 314 to determine appropriate initial recommendations. The knowledge base consists of a set of dosage rules that provides the recommended initial dosages in different situations for different users as well as rules to support dosages based on user feedback, aggregated user data, and dosage history. For instance, if a user needs vitamin C, there would a recommended daily dosage based on the user's profile. In one or more embodiments, a health care professional can be provided with the recommendation for approval prior to presentation to the user. In other embodiments, the knowledge base can be configured to use proprietary or public medical and nutritional databases to derive the rules. In one or more embodiments, the dosage rules recommendations can be reviewed by an outside party. In or more embodiments, the knowledge base is configured to accept rule edits and additions from a designated third party.

Figure 16:
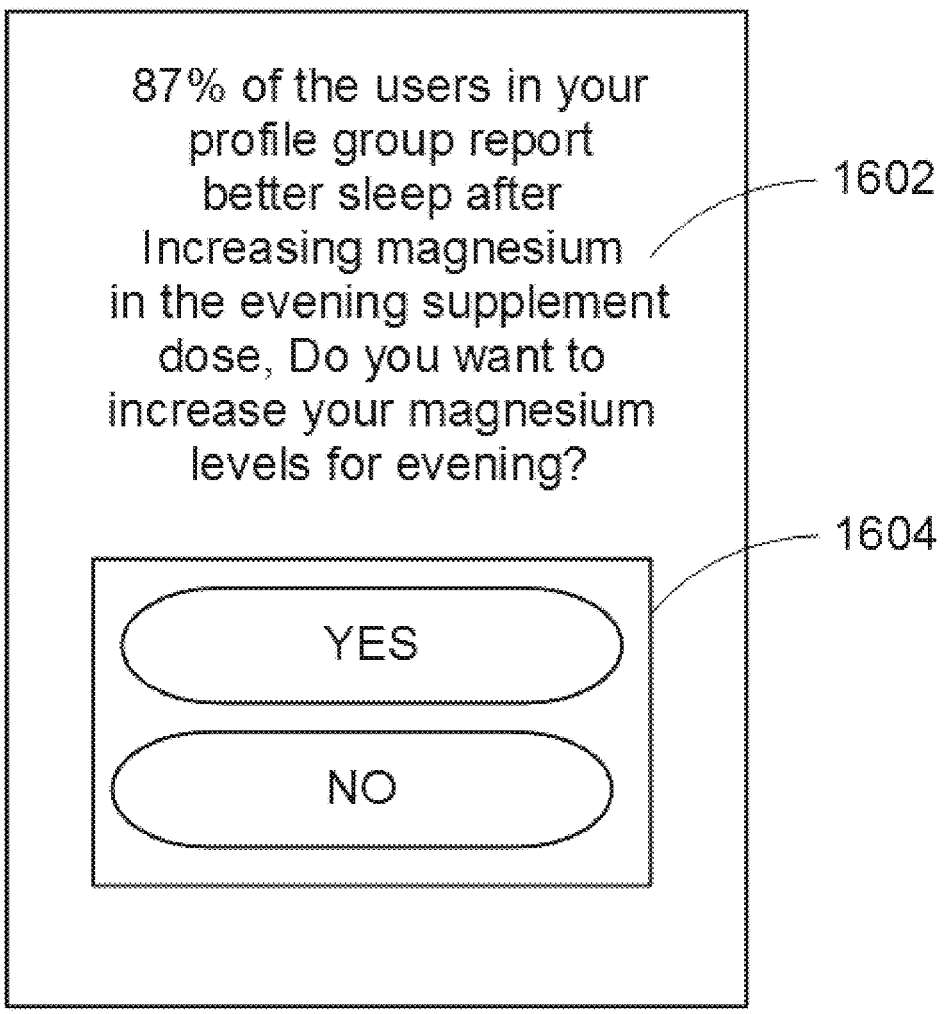
FIG. 16 shows one or more embodiments of encouraging a display used to encourage a user to take a dosage by showing them how similar users responded to the dosage.

In one or more embodiments, data is collected from users and users are grouped by user profile information using such characteristics as similar age group, weight group, gender and height. When presenting users with an option to take a new dosage, a display such as shown in FIG. 16 can be presented to them. In one or more embodiments, the data is used by the Recommendation Engine to determine whether it is valuable to alter the user's dosage, based on responses of other similar users. A message is displayed to the user showing how other users in their profile group responded to the recommended dosage 1602. The user is then given the option of accepting or rejecting the recommendation 1604.

In one or more embodiments, the Recommendation Engine 314 can be used to adjust the user's dosage on a regular basis for optimum results that might discourage a user from taking the dosage without really harming them, such as temporary rashes and facial flushing. This is done using a technique we call titration, which is similar to medical titration, in that the dosage is adjusted to achieve optimal results. Based on user feedback, the Recommendation Engine can adjust the substance mix, time of dosage, quantity of dosage, and frequency of dosage, for each recommendation. In one or more embodiments, the knowledge base contains rules that state when a dosage should be recommended to be changed based on user feedback, dosage history, and user profile, using the parameters of titration.

It should also be understood that one or more embodiments of this apparatus can be used to manage pharmaceuticals, such that the Recommendation Engine 314 is configured to interact with one or more designated medical personnel to obtain approval and/or modification of the dosages.

In one or more embodiments, the mobile compute device 210 is also configured to accept messages from users 202 and other sources 214 providing information about the user's health and wellbeing over time. This information from can come from other sources such as wearable devices, health monitoring devices, user feedback, databases which track the health and wellness of users, and the results of medical tests. In one or more embodiments, this information can be part of the order request 208.

Figure 3:
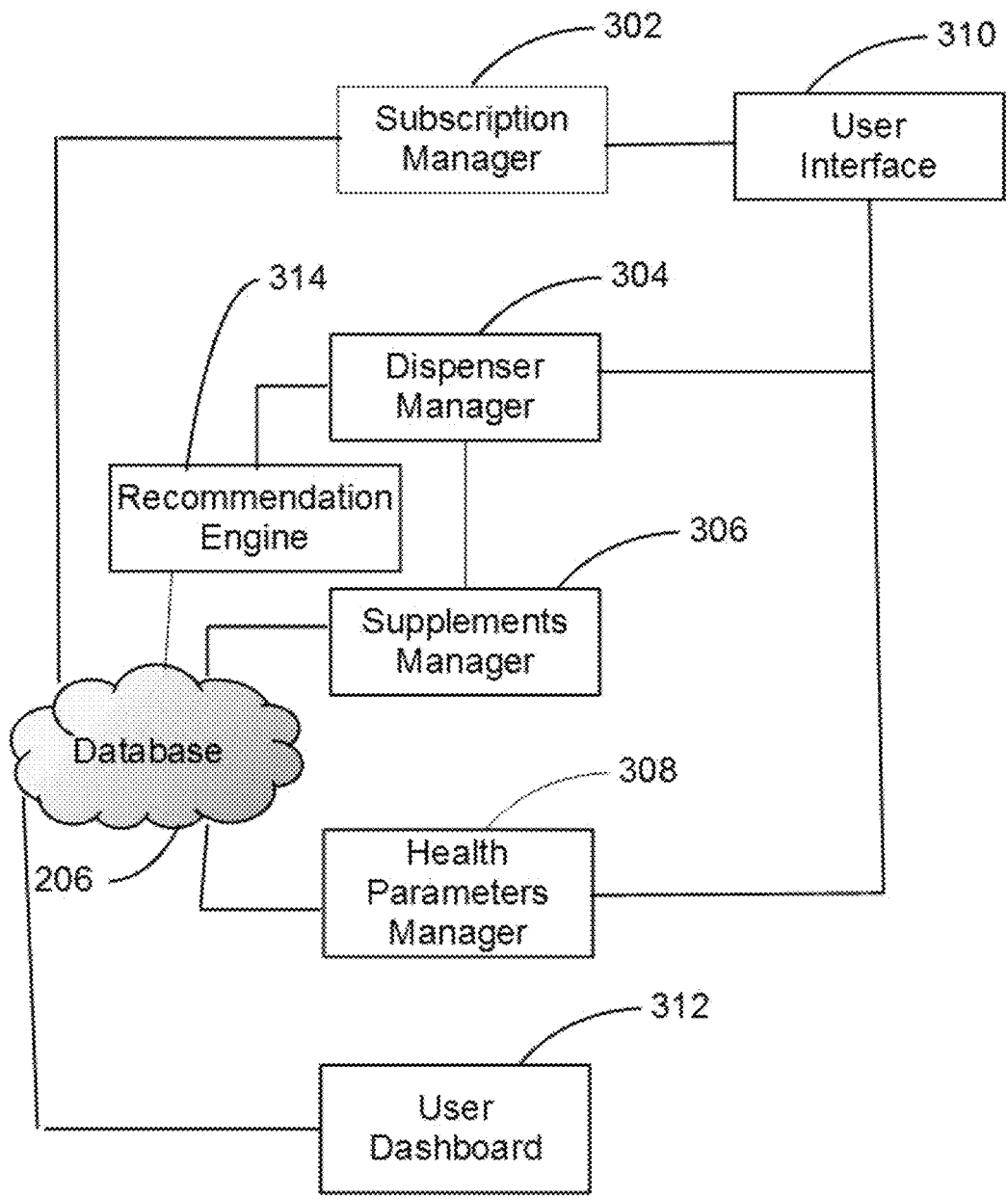
FIG. 3 shows an embodiment of the architecture of the software modules associated with the apparatus.

FIG. 3 shows an embodiment of the modules required to execute one or more embodiments of the workflow of the apparatus.

In one or more embodiments, the User Interface Module 310 controls access to the subscription, dispenser, and health parameter information.

In one or more embodiments, the Subscription Manager 302 determines whether a user has a subscription via the User Interface Module 310, and if not, the Subscription Manager 302 prompts the user to create a subscription. The Subscription Manager 302 accepts registration, payment and login information from a user such as name, email id, date of birth, sex, credit card, and Facebook login. The resulting subscription information is stored in the database 206. In one or more embodiments, the subscription information is used to create initial user profile information.

In one or more embodiments, the Dispenser Manager 304 notifies the user via the User Interface 310 or some alternate means such as messaging when it is time to take a dose, accepts the users request to dispense the dose as a mixture of one or more dietary supplements and/or drugs, and send a message that the user is ready to take the dosage 204 to an external system. It also accepts a response confirming that the dose was taken 212.

Figure 8:
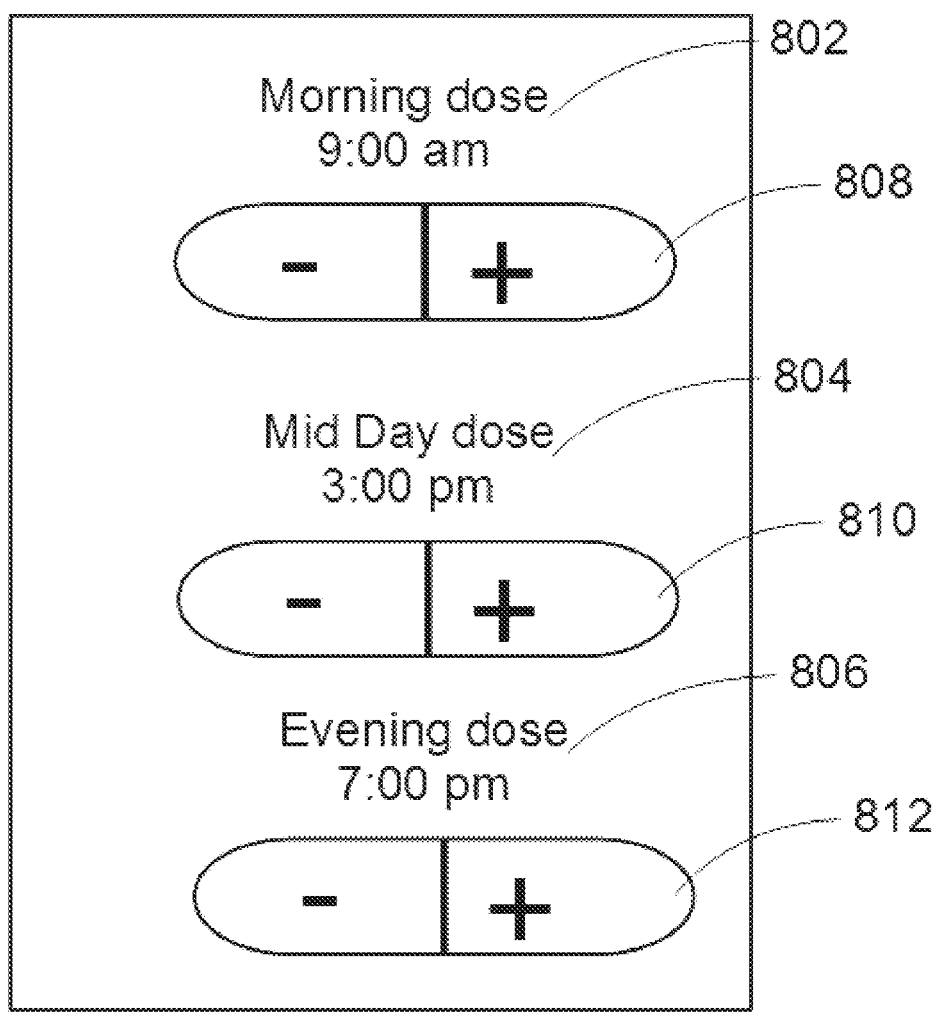
FIG. 8 shows one or more embodiments of a display to select dosage times.

In one or more embodiments, the user can adjust his or her schedule using a user interface as shown in FIG. 8. In one or more embodiments, one or more dosages can be scheduled from a single screen. In the embodiment shown, the morning dose time 802 is displayed and can be adjusted 808 by the user. The mid-day dose time 804 is displayed and can be adjusted 810 by the user. The evening dose time 806 is displayed and can be adjusted 812 by the user.

Figure 9:
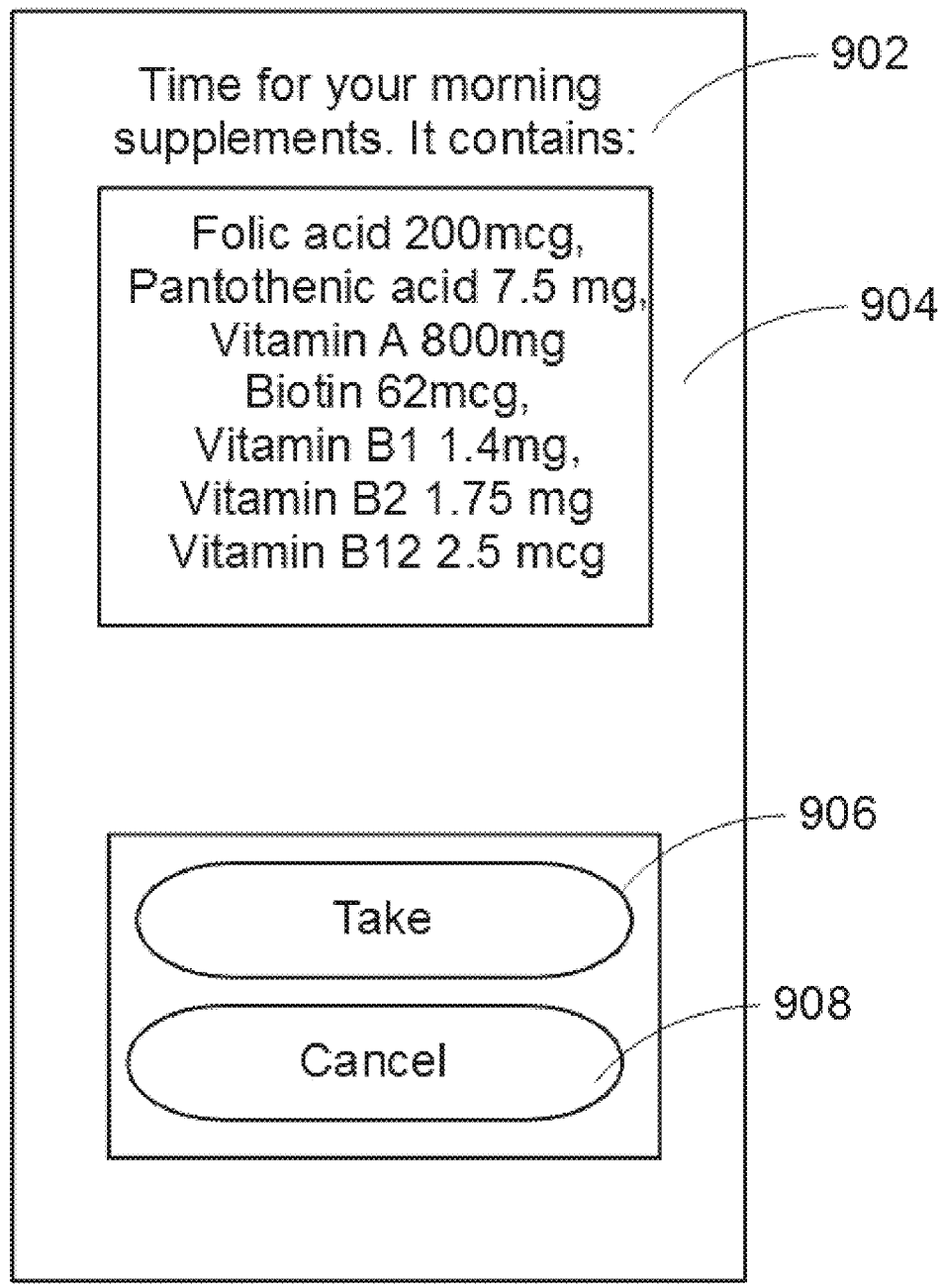
FIG. 9 shows one or more embodiments of a display to notify a user that it is time to take a dose.

In one or more embodiments, the Supplements Manager 306 tracks the amount of each product that is required for a dose and, through the Dispenser Manager 304, how much of each product is estimated to be available. In one or more embodiments, a user interface is displayed to the user when it is time to take a dosage, as shown in FIG. 9. In one or more embodiments, the user is alerted as to what dosage this is 902, the drug-based or dietary supplement products contained in the dose, and/or value to the user of the dosage 904 The user is then presented with the option to take 906 or cancel 908 the dosage. In one or more embodiments, when the user selects the take button 906 the Dispenser Manager 304 is configured to accept a message from the user interface that the user is ready to take the dosage 204.

When the Dispenser Manager 304 receives a message that a dosage has been dispensed 212, it notifies the Recommendation Engine 314 and the Supplements Manager 306. The Supplements Manager 306 tracks how much of each drug-based or dietary supplement product was ordered via the database 206, and is forwarded the message from the Dispenser Manager 304 when a product order has been received 212. From how much was ordered and how much was used since a product was replenished, the Supplements Manager 306 estimates how much of each product remains and can calculate when each product will run out. In one or more embodiments the Supplement Manager 306 can be configured to report to an external order system when a specified number of days remain for a given product. In one or more embodiments, the Supplements Manager 306 can accept requests to adjust the dose, at which time the Supplements Manager 306 can notify the Dispenser Manager 304 of the dosage change.

In one or more embodiments, the User Interface Module 310 can accept requests from users for an on-demand dosage and present a user with options such as "improve focus", "stay awake", "go to sleep". The User Interface Module 310 would then communicate with the Supplements Manager 306 and the Dispenser Manager 304 to affect the release of the on-demand dose.

By "on-demand" dosage, we are referring to the ability for a user to request a specific dose given for a user-perceived need at a user-specified time. In one or more embodiments, the mobile apparatus is also configured to accept notifications that the user took a dosage from an external system.

Figure 13:
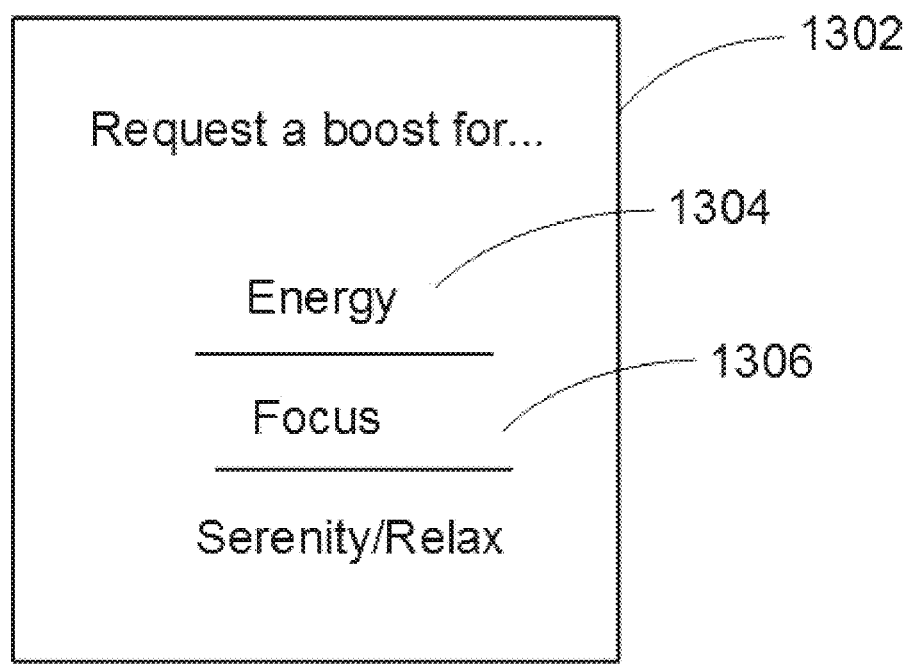
FIG. 13 shows a display to allow a user to request an on-demand dosage for one of several reasons.

FIG. 13 shows a display to allow a user to request an on-demand dose for one of several reasons. In one or more embodiments, the display will prompt the user to request a boost 1302, give them the list of boost options 1304, and allow them to select one of the boost options 1306.

In one or more embodiments, the Health Parameters Manager 308 is configured to accept general information about the user (age, weight, sex, allergies) from the User Interface 310, to prompt the user and accept information from the user on a periodic basis about changes in his health and well-being, and to accept information from one or more external devices via the other software or hardware devices. One instance of such external software would be the Apple Health Kit. In one or more embodiments, the Health Parameters Manager 308 would be configured to integrate with Bluetooth devices such as a FitBit. In one or more embodiments, the Health Parameters Manager 308 is configured to accept medical information from an electronic medical record. The information gathered by the Health Parameters Manager 308 is stored in the database 206 and can be sent as part of the order message 208.

In one or more embodiments, a User Dashboard 312 is configured to accept health, dosage makeup and frequency, and subscription information from the database 206 and display it to the user on request. In one or more embodiments, the User Dashboard 312 can display trends in wellness, the user's record of taking doses on schedule, and health information derived from the user input and external software or hardware. For example, in one or more embodiments the User Dashboard 312 will show that a certain percentage of users who have the same or similar characters of this user have had optimum results while using a specific dosage. In one embodiment, the User Dashboard 312 displays a calendar showing what dosages were taken, when they were taken, and when user feedback was provided. In one or more embodiments, the User Dashboard 312 would display collective feedback from users either based on who took the dosage and whether they were able to meet the specific goal of the user (wakefulness, feeling of general well being, etc). In other embodiments, the collective feedback could be limited to a class of similar users using such criteria as age, gender, and weight.

Figure 11:
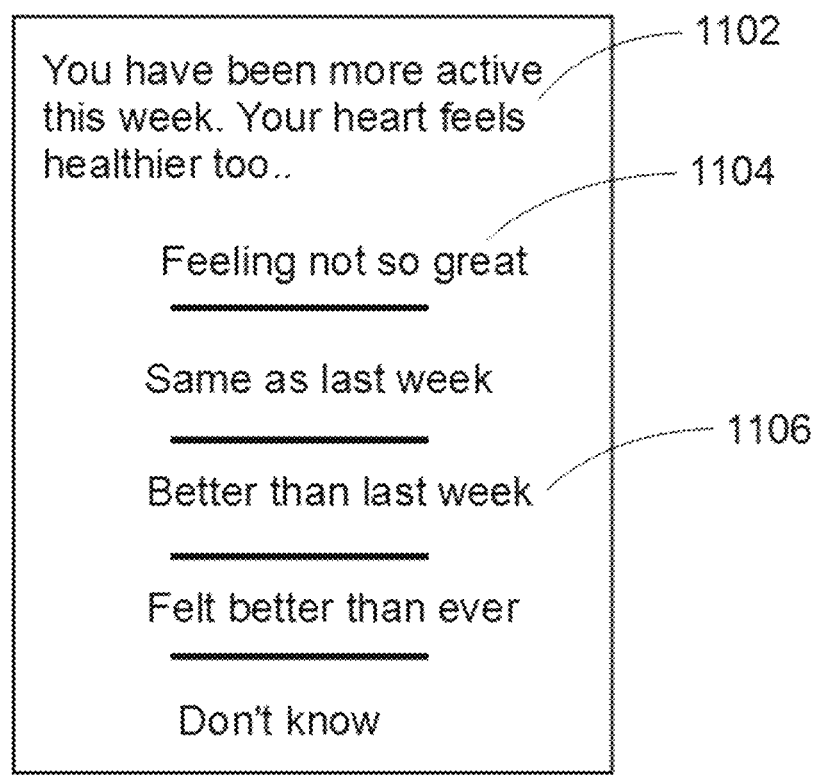
FIG. 11 shows one or more embodiments of a display to request feedback from a user.

In one or more embodiments, the user feedback could take the form of a questionnaire. FIG. 11 shows an example of a short questionnaire. The user is provided with a statement 1102 and one or more possible responses 1104. The user can select one of those responses 1106. The system then records the response in the database 206, which can then be used by the Recommendation Engine 314 to determine whether the dosage should be adjusted.

In one or more embodiments, the User Interface Module 310 is configured to provide encouragement in the form of setting expectations for the user as to what kinds of effects they should see, when they should see those effects, and how those effects will improve with a consistent dosage history.

In one or more embodiments, the User Interface Module 310 is configured to provide encouragement in the form of rewards for adherence to the taking of supplements or rewards for providing regular user feedback. In other embodiments, the User Interface Module 310 is configured to provide encouragement to the user in the form of virtual badges, and posting messages to various social network sites on the user's behalf touting his progress. In one or more embodiments, the rewards can also include discounts on subscriptions or early access to new products.

Figure 12:
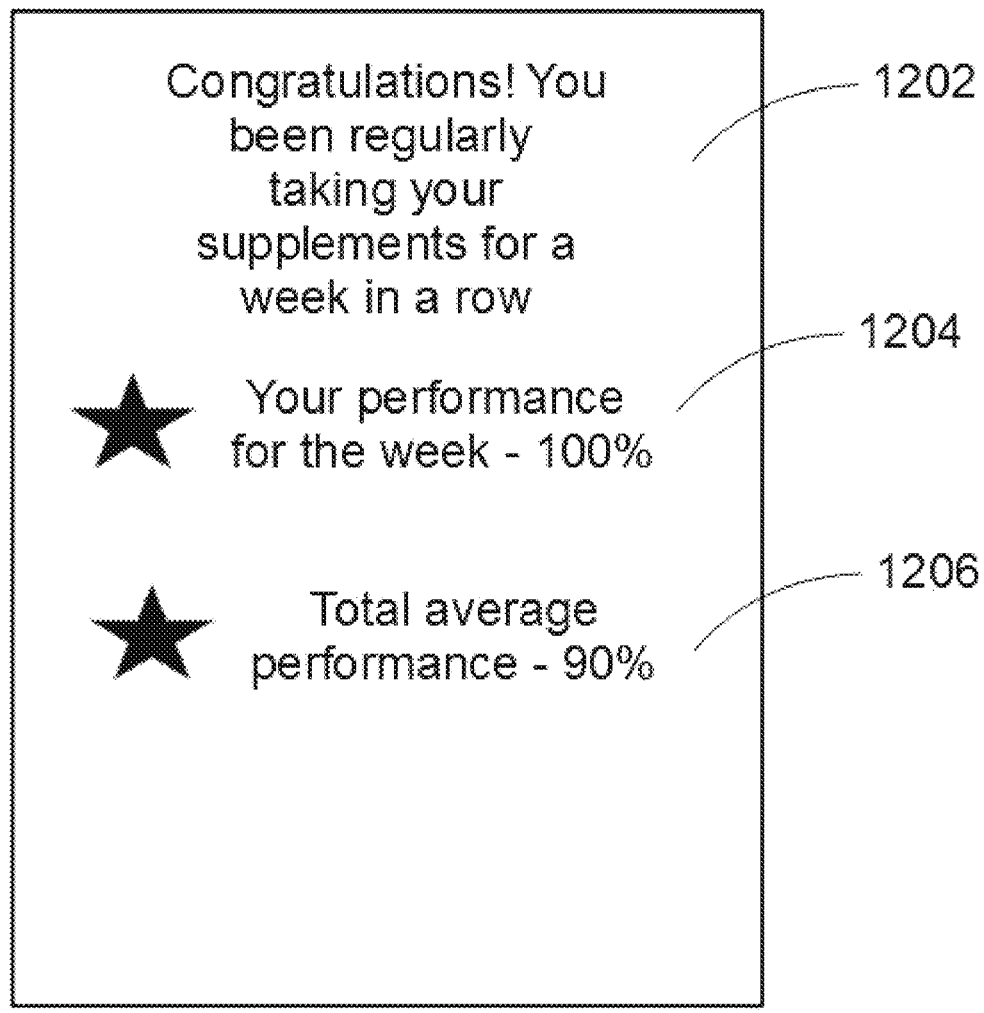
FIG. 12 shows one or more embodiment of general encouragement to a user based on their overall adherence to the dosage schedule.

FIG. 12 shows one or more embodiment of general encouragement to a user based on their overall adherence to the supplement schedule. In one or more embodiments, the display will show a general encouragement message reminding a user that they have been adhering to the program for some period of time 1202. In one or more embodiments, it may also display how their performance has been for some fixed period like the last week or last month 1204, along with their average performance since they started taking supplements 1206.

In one or more embodiments, the encouragement is based on how a user should feel based on their usage pattern. For example a certain dietary supplement or drug might improve the users sleep pattern after taking it regularly for a week. In that case we would display to user the time to meet their goal based on their actual usage.

In one or more embodiments, the apparatus provides encouragement to the user in the form of helping them understand that the changes they will experience when they take supplements may not be instantaneous and that they will vary from user to user. There are affects they may experience after a short period of minutes or hours taking a single dose, then there are affects they may experience after taking a series of dosages over a period of days or weeks.

Figure 14:
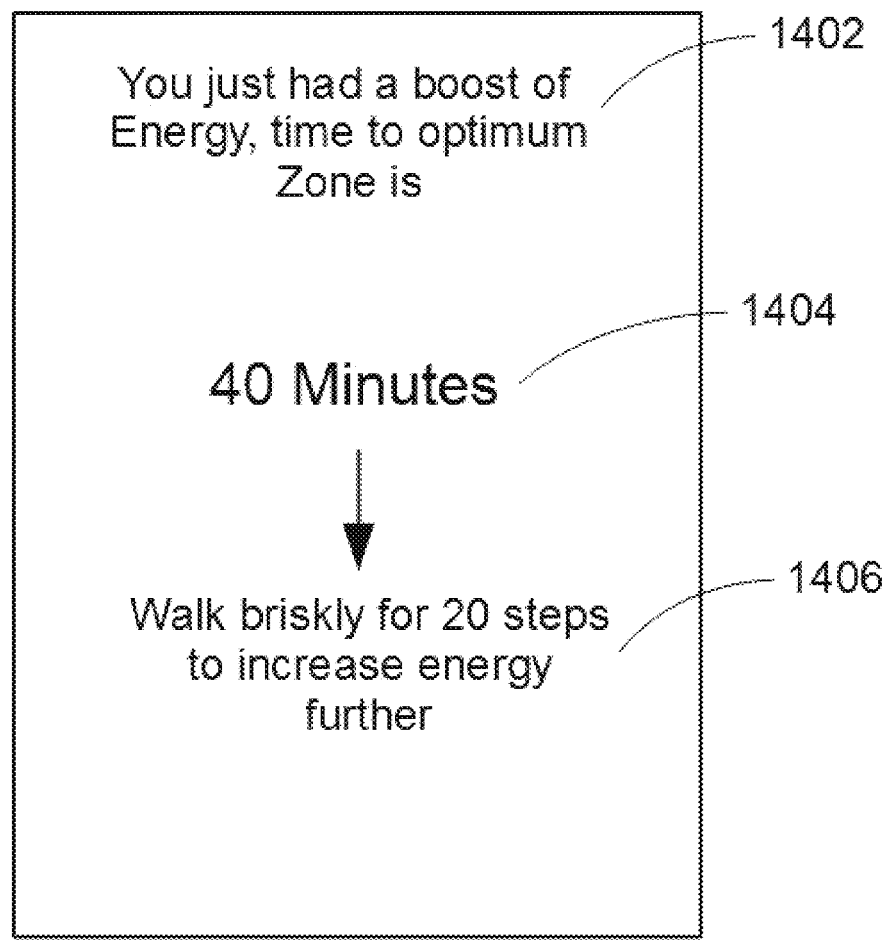
FIG. 14 shows one or more embodiments of a display to provide a user encouragement after taking a single dosage.

FIG. 14 shows an embodiment of a response to a user taking a dosage. First, the display confirms what the user took and what the expected kind of response will be 1402. Next it will display an indication of when this effect should be felt 1404. Finally it makes recommendations as to what users of this dosage have done to improve the effects of the dosage 1406.

Figure 15:
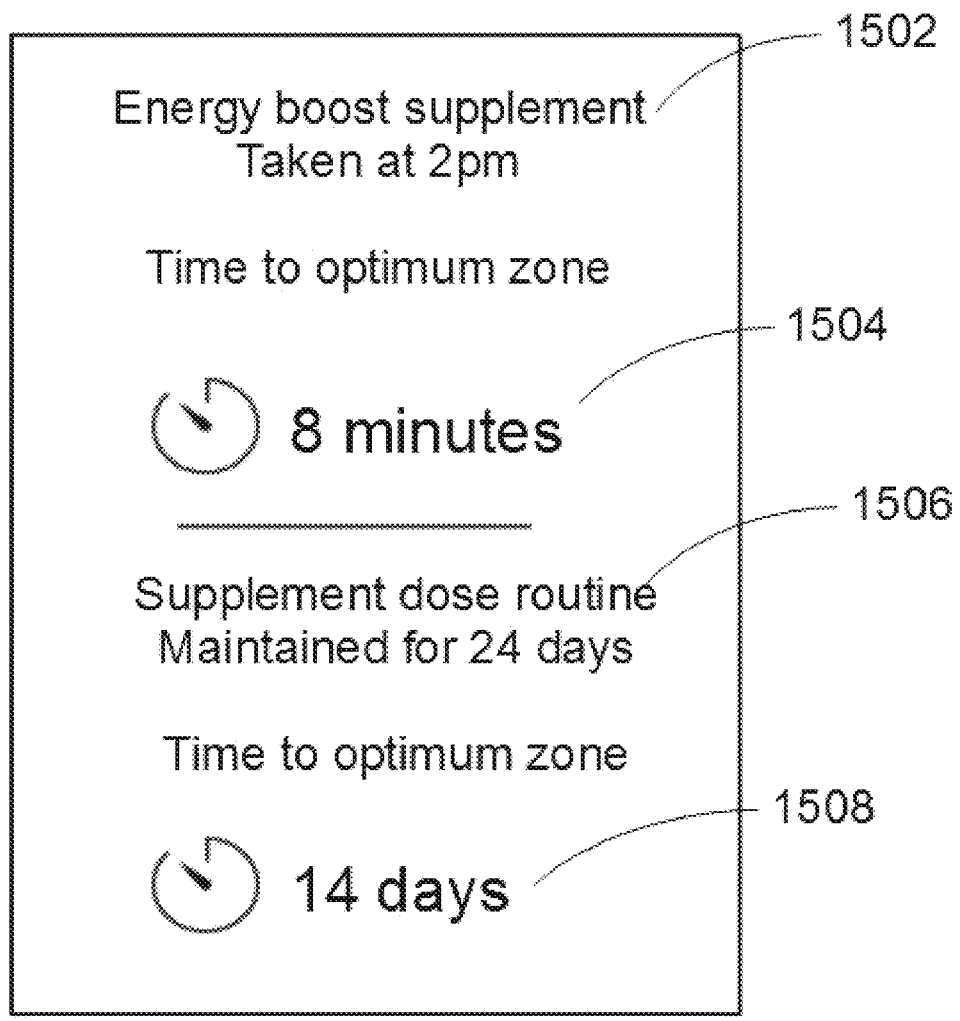
FIG. 15 shows one or more embodiments of a display to provide a user with encouragement after taking a series of dosages.

FIG. 15 shows an embodiment of a response to user taking a series of dosages. First, the display confirms what the user took and what the expected kind of response will be 1502. Next it will display an indication of when this effect should be felt 1504. Then, the display shows the user how long they have been taking the dosage consistently 1506 and an estimate of how long it will be before it will have its optimal effects on them 1508. In one or more embodiments, this estimate is calculated by comparing the user profile data to knowledge base and other users with a correlated profile and what their feedback was. User profile data is correlated with another user's profile if those users are in the same or similar profile group. That is, taking a range of ages, weight, height, gender, and general health into consideration as available. For instance, if a 50-year-old male user is taking a dosage, one could correlate the user feedback data from other male users in the 45-55 age range of similar height and health.

Figure 4:
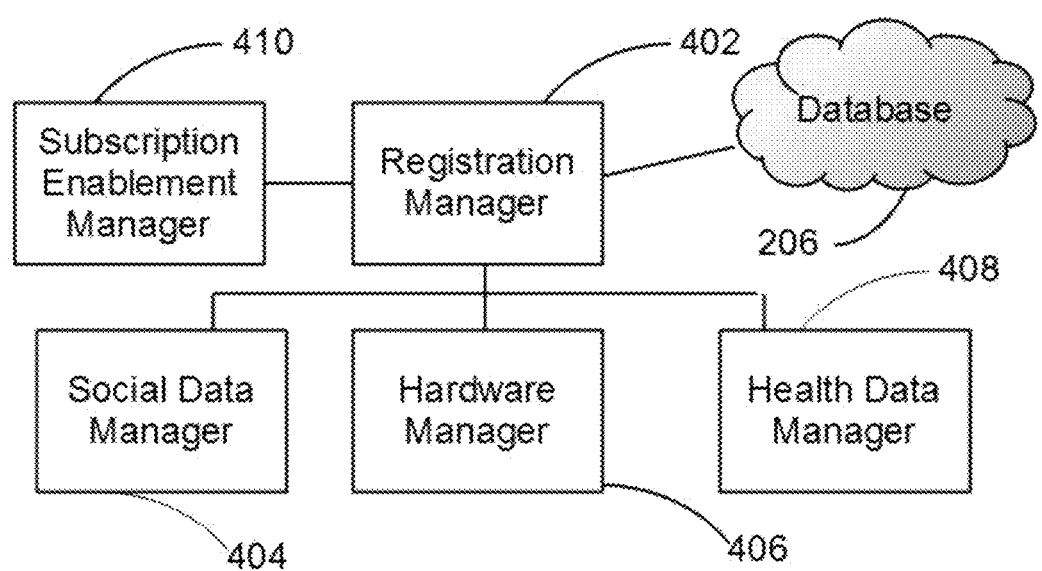
FIG. 4 shows an embodiment of the subscription software.

FIG. 4 shows an implementation of one or more embodiments of the Registration Module. In one or more embodiments, the registration module gathers information about the user and enables his/her subscription to the service. The Registration Manager 402 controls the workflow to establish a logical sequence of steps for the user. The user is prompted for personal data. In one or more embodiments, this is accomplished by mining data from one or more social media sites via the Social Data Manager 404. The user is prompted to provide access information for one or more social media sites, such as Facebook, and data is then gleaned from the user profile information. In other embodiments, the user is presented with a form to enter such information as name, residence, gender, age, and marital status, if social media information is unavailable or incomplete. The Hardware Manager 406 establishes permission from the user to mine hardware information from a mobile compute device 210. In one or more embodiments, this would include GPS, motion sensors, clock, accelerometers, compass, gyroscopes, and barometers. Each of these devices could enable the apparatus to monitor the health of the individual carrying the mobile compute device. For instance, the hardware that work to detect motion and position such as GPS and accelerometer can be used to detect motion on the part of the individual carrying the device, which can translate to exercise. The clock is needed to be able to alert the user when it is time to take a supplement, as well as to timestamp when the user is requesting or receiving supplements.

As another step in the registration workflow, the Registration Manager presents the user with information needed to enable a subscription, which is done via the Subscription Enablement Manager 410. In one or more embodiments, this would be credit card information or other source of credit such as PayPal. In other embodiments, it could be insurance or health plan information.

The data from the registration process is stored in a database 206. The database may be on the mobile computer device, at a remote site, or both. In one or more embodiments, the registration information can be used to recommend an initial regimen of supplements. In other embodiments, more detailed health information would be included or requested to determine if allergies, lifestyle issues, chronic illnesses or personal goals should be taken into account, according to the supplements available.

In one or more embodiments, the user interacts with the Health Data Manager 408 and gives the application permission to access one or more mobile compute device's databases via such External APIs as Apple Health Kit or the Google Fit API. External APIs provide a source of health information that can be used to determine the current status of a user, which can then be used by the Recommendation Engine 510 to determine a proper dosage based on mixture of one or more products, amount of product in each dosage, and frequency of dosage.

Figure 5:
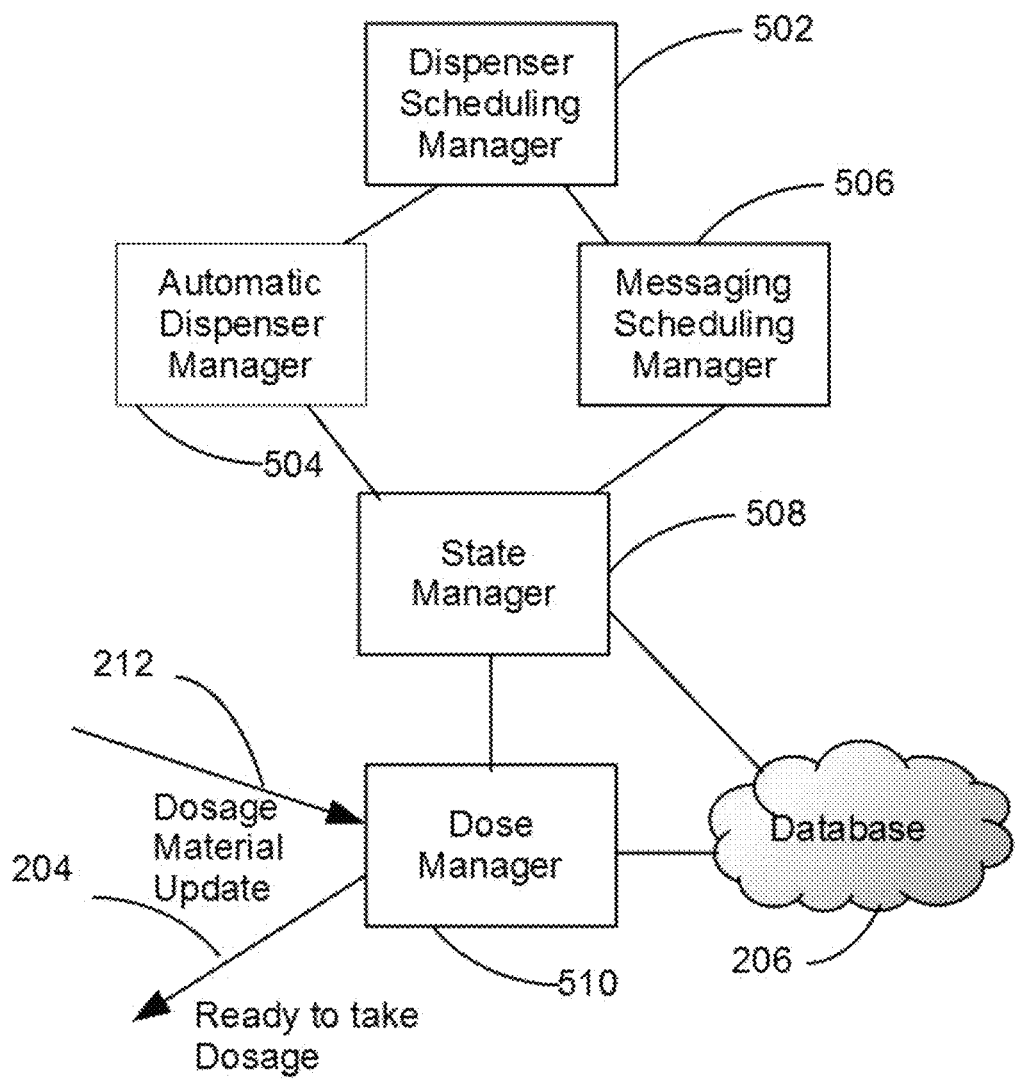
FIG. 5 shows an embodiment of the dispenser module.

FIG. 5 shows an implementation of one or more embodiments of the Dispenser Manager Module. The Dispenser Scheduling Manager 502 accepts requests for scheduled or on-demand dosages. In one or more embodiments, the Automatic Dispenser Manager 504 accepts requests for dosages on a periodic basis. In one or more embodiments, the Messaging Scheduling Manager accepts asynchronous requests for a dosage. This could be to help the user relax, give him/her a boost of energy or alertness. In one or more embodiments, the Messaging Scheduling Manager 506 can accept requests via a UI or a text message.

In one or more embodiments, the Dispenser Manager Module 502 is configured to accept notifications that the user took a dosage and as a result update the dosage history and the amount of material available. In one or more embodiments the notifications are triggered by a user action. In other embodiments the notifications are triggered by an external system.

Once a request for a dosage has been received, either synchronously through the Automatic Dispenser Manager 504 or asynchronously through the Messaging Scheduling Manager 506, the State Manager 508 gathers the current state of the user via the mobile compute device hardware, the various available APIs such as the Apple Health Kit, and data stored in the database 206. This information is sent to the Dose Manager 510 from the Recommendation Engine 314, which in one or more embodiments determines the proper dose to dispense and sends the ready to take dosage message 204. The Dose Manager 510 is also configured to receive the Dosage Material Update message 212, the information from which is used to update the database 206 with the date, time, and dosage if it was a decrease in one or more products (which is assumed to mean that a dose was taken), or to reset the current level of one or more products if it was an increase in the amount of one or more products.

In one or more embodiments, the Recommendation Engine 314 leverages the information provided by the dosage history, the adherence of the user to the dosage schedule, the user feedback and the health information to send information to the Dose Manager 510 to adjust the user dosage as needed. In one or more embodiments, the Recommendation Engine 314 would suggest an on-demand dosage as dictated by circumstances. In one embodiment, the Recommendation Engine 314 would suggest a dose of dietary supplement or drug-based products to help wakefulness when a person is awake for a longer period than they normally would be, or upon changing time zones to help them with jet lag. In other embodiments, a User would request an off-schedule dosage for a particular reason, such as helping them to stay awake, help them sleep, or help them focus. In one or more embodiments, the Dose Manager 510 would calculate an acceptable dose of products for a boost. In one or more embodiments, the Dose Manager 510 would limit user selected or other recommended extra dosages based on limits on the amount of specific dietary supplement and drug products over some period of time.

Figure 6:
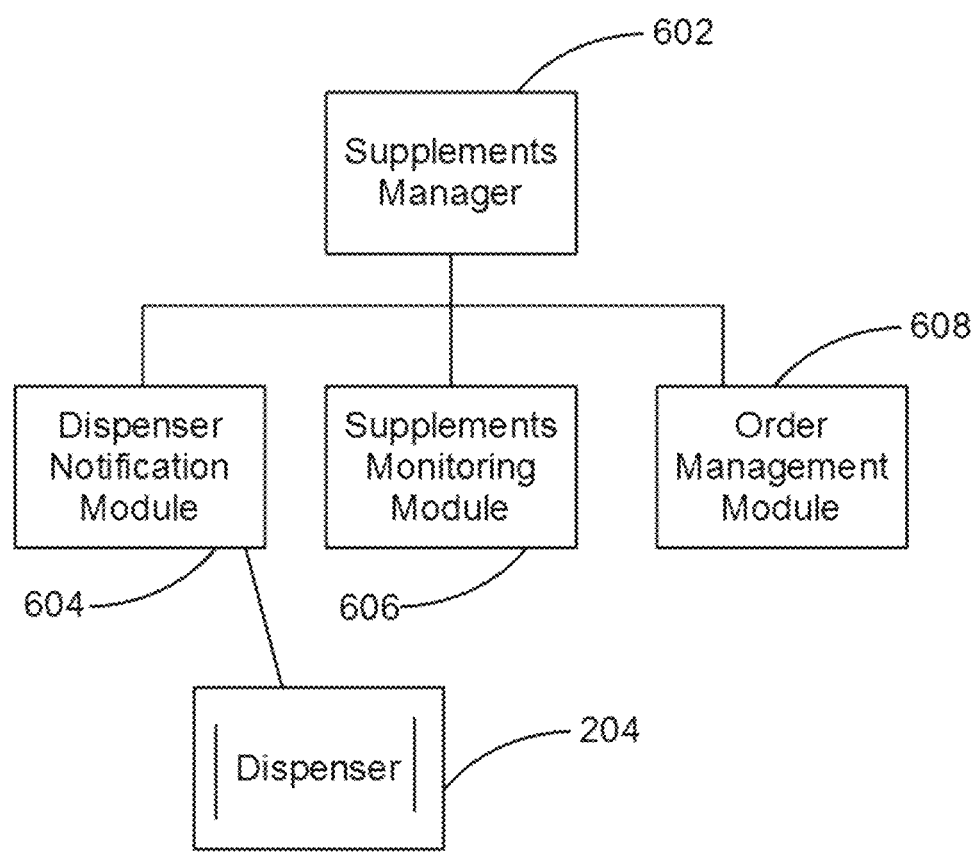
FIG. 6 shows an embodiment of the dosage management software.

FIG. 6 shows an implementation of one or more embodiments of the Supplements Module. The Supplements Manager 602 coordinates the flow between the monitoring of available products and the ordering of products. The Dispenser Notification Module 604 accepts notifications when a mixture of products have been dispensed or when newly ordered products have been received and are ready to be taken 204. The Supplements Monitoring Module 606 calculates the current amount of products available and determines when a new order should be placed. In one or more embodiments, the residence and/or location of the user as determined by the location information from the mobile compute device 210 or a user-provided address is taken into consideration, based on the time to deliver a new container of product to the user. The rate of dosage history is also used, such that it is estimated that there will be adequate products available until the order is supposed to arrive. In one or more embodiments, the Order Management Module 608 accepts requests to place an order for one or more products.

Figure 7:
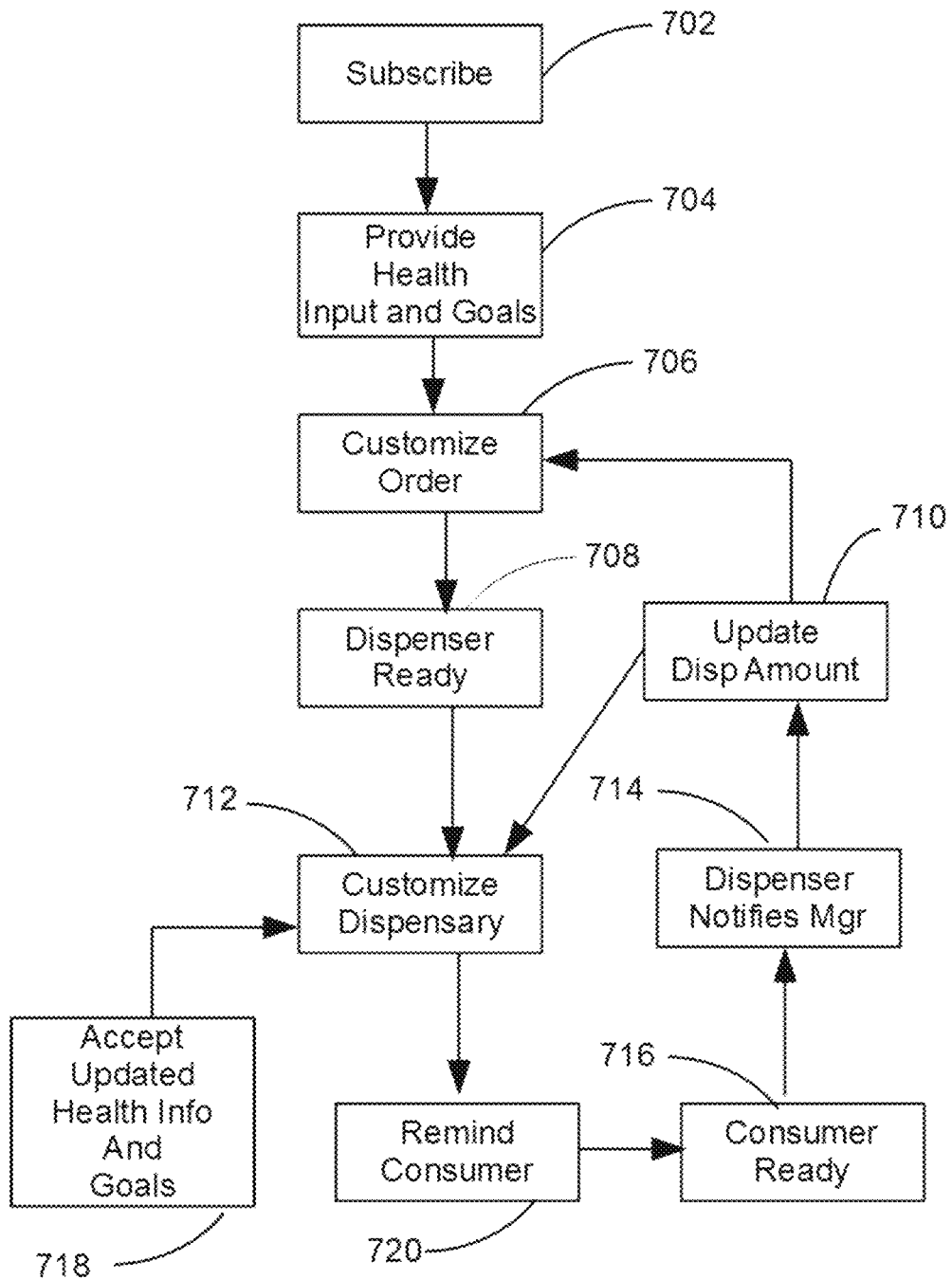
FIG. 7 shows an embodiment of a workflow process associated with the apparatus.

One or more embodiments of the workflow associated with the apparatus is shown in FIG. 7. A user is prompted to subscribe 702 and an account is setup for the user. In one or more embodiments, the user is presented with a form to enter basic information including personal information such as name, birthday, sex and email. In other embodiments, the user can share a login from a social network such as Facebook. Some of the information can be gleaned from their profile there, the rest added to the medical questionnaire as needed.

Once the user has subscribed, the system interacts with the user to gather basic health information and obtain the user's personal goals towards improving his health and wellbeing 704. In one or more embodiments, the system interacting with the user would include having a user answer a questionnaire. In one or more embodiments the user profile information would include physical information, personal habits that might affect the person's health such as drinking and smoking, exercise regimen, diet, and sleep quality.

In one or more embodiments, the user would also be asked for authorization to access real-time information from personal monitoring devices, health wearables, and other connected devices.

Based on the initial inputs, a request is sent to order one or more products 208.

In one or more embodiments, the Supplements Manager 306 accepts a message confirming the order. The Supplements Manager is also configured in one or more embodiments to accept a message 212 that the ordered products are available for dispensing 708.

Based on the received order, an initial dose is defined, but this can be customized over time 712 based on updated health information and personal goals 718. Once the apparatus has accepted the message that the products are ready to be dispensed, the user has accepted the dose and timing of the dose, it can notify the user on a periodic basis when it is time to take a particular dose 720. The mobile apparatus can accept a notification from a user when the user is ready 716, and send a message when the user is ready to take the dose 714. The apparatus can then accept a message that the dose was dispensed, and update the amount of each product it estimates is available 710.

In one or more embodiments, programming instructions for executing above described methods and systems are provided. The programming instructions are stored in a computer readable media.

With the above embodiments in mind, it should be understood that one or more embodiments of the invention may employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations described herein that form part of one or more embodiments of the invention are useful machine operations. One or more embodiments of the invention also relates to a device or an apparatus for performing these operations. The apparatus may be specially constructed for the required purposes, such as the carrier network discussed above, or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

The programming modules and software subsystems described herein can be implemented using programming languages such as Flash, JAVA™, C++, C, C#, Visual Basic, JavaScript, PHP, XML, HTML etc., or a combination of programming languages. Commonly available protocols such as SOAP/HTTP may be used in implementing interfaces between programming modules. As would be known to those skilled in the art the components and functionality described above and elsewhere herein may be implemented on any desktop operating system such as different versions of Microsoft Windows, Apple Mac, Unix/X-Windows, Linux, etc., executing in a virtualized or non-virtualized environment, using any programming language suitable for desktop software development.

The programming modules and ancillary software components, including configuration file or files, along with setup files required for providing the method and apparatus for troubleshooting subscribers on a telecommunications network and related functionality as described herein may be stored on a computer readable medium. Any computer medium such as a flash drive, a CD-ROM disk, an optical disk, a floppy disk, a hard drive, a shared drive, and storage suitable for providing downloads from connected computers, could be used for storing the programming modules and ancillary software components. It would be known to a person skilled in the art that any storage medium could be used for storing these software components so long as the storage medium can be read by a computer system.

One or more embodiments of the invention may be practiced with other computer system configurations including hand-held devices, microprocessor systems, microprocessor-based or programmable consumer electronics, minicomputers, mainframe computers and the like. The invention may also be practiced in distributing computing environments where tasks are performed by remote processing devices that are linked through a network.

One or more embodiments of the invention can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, DVDs, Flash, magnetic tapes, and other optical and non-optical data storage devices. The computer readable medium can also be distributed over a network coupled computer systems so that the computer readable code is stored and executed in a distributed fashion.

While one or more embodiments of the present invention have been described, it will be appreciated that those skilled in the art upon reading the specification and studying the drawings will realize various alterations, additions, permutations and equivalents thereof. It is therefore intended that embodiments of the present invention include all such alterations, additions, permutations, and equivalents as fall within the true spirit and scope of the invention as defined in the following claims. Thus, the scope of the invention should be defined by the claims, including the full scope of equivalents thereof.

We claim:

1. A method for monitoring consumption of dietary supplement products, the method comprising:
   accessing a set of characteristics of a user at a first time;
   identifying a group of users, in a population of users, exhibiting characteristics similar to the user based on the set of characteristics of the user;
   retrieving a dosage history and feedback for the product, submitted by the group of users, from a set of databases;
   at a recommendation engine, calculating a dosage amount of a product for the user based on the dosage history and feedback for the product from the group of users;
   initiating a dosage schedule for the product in the dosage amount for the user;
   at a dispenser manager, transmitting a prompt, to consume a dose of the product in the dosage amount, to the user via a computing device based on the dosage schedule;
   accessing a confirmation of consumption of the dose of the product entered by the user at the computing device;
   accessing a description of an expected effect of the dose of the product from the set of databases;
   at a user interface module, estimating a time to the expected effect felt by the user based on the confirmation of consumption of the dose of the product by the user and feedback for the product from the group of users; and
   in response to the confirmation of consumption of the dose of the product by the user, presenting to the user, via the computing device, the description of the expected effect and the time to the expected effect felt by the user.

2. The method of claim 1, further comprising:
   calculating a current amount of the product available to the user based on the confirmation of consumption of the dose of the product by the user; and
   sending a message to order more of the product in response to the current amount of the product falling below a threshold number of doses of the product.

3. The method of claim 1, wherein transmitting the prompt to the user to consume the dose of the product comprises, rendering on a display of the computing device:
   the prompt to consume the dose of the product; and
   a description of responses to consumption of the product, in the dosage amount, by users in the group of users.

4. The method of claim 1, further comprising:
   accessing an action by users, in the population of users, concurrent with consumption of the product to increase the expected effect; and
   in response to the confirmation of consumption of the dose of the product by the user, rendering, on a display of the computing device, a recommendation to perform the action to increase the expected effect felt by the user.

5. The method of claim 4:
   wherein accessing the description of the expected effect of the dose of the product comprises accessing the description of the expected effect comprising a perceived energy increase;
   wherein estimating the time to the expected effect felt by the user comprises estimating the time to a period of the perceived energy increase by the user based on the confirmation of consumption of the dose of the product by the user; and
   wherein rendering, on the display, the recommendation to perform the action comprises rendering, on the display, the recommendation to walk briskly to increase the perceived energy increase in response to the confirmation of consumption of the dose of the product by the user.

6. The method of claim 1:
   wherein estimating the time to the expected effect felt by the user comprises:
     accessing a consumption history of the product by the user;
     calculating an adherence to the dosage schedule by the user based on the consumption history; and
     estimating a number of days to optimum magnitude of the expected effect, of the product, felt by the user based on the adherence to the dosage schedule; and
   wherein presenting to the user, via a display of the computing device, the time to the expected effect felt by the user comprises rendering, on a display of the computing device, the number of days to optimum magnitude of the expected effect felt by the user.

7. The method of claim 6:
   wherein retrieving the dosage history and feedback for the product, submitted by the group of users, from the set of databases comprises:
     accessing a consumption history of the product by the group of users; and
     accessing feedback from the group of users following consumption of the product; and
   wherein estimating the number of days to optimum magnitude of the expected effect comprises estimating the number of days to optimum magnitude of the expected effect felt by the user based on the adherence to the dosage schedule, the consumption history of the product by the group of user, and feedback from the group of users.

8. The method in claim 7, further comprising:
   detecting an exigent circumstance experienced by the user;
   generating a recommendation for an off-schedule dosage of a second product associated with a second effect related to the exigent circumstance;
   estimating a time to the second effect felt by the user responsive to consumption of the off-schedule dosage of the second product; and
   presenting the recommendation and the second time to the second effect felt by the user via a display of the computing device.

9. The method of claim 1:
   further comprising:
     serving a set of effects to the user via a display of the computing device;
     prompting the user to select an effect from the set of effects; and
     identifying the product in response to selection of the expected effect from the set of effects by the user; and wherein calculating the dosage amount comprises calculating the dosage amount for the product in response to selection of the expected effect from the set of effects by the user.

10. The method of claim 1:
wherein accessing the set of characteristics of the user comprises:
serving a survey to the user via a display of the computing device; and
accessing a wellness-related goal entered into the survey by the user;
further comprising identifying the product associated with the expected effect linked to the wellness-related goal entered by the user; and
wherein calculating the dosage amount comprises calculating the dosage amount for the product based on the wellness-related goal entered by the user.

11. The method of claim 10, further comprising:
at a second time, receiving a modification of the wellness-related goal from the user;
recalculating the dosage amount for the product based on the modification of the wellness-related goal entered by the user; and
updating the dosage schedule for the product responsive to the modification of the wellness-related goal.

12. The method of claim 1:
wherein accessing the set of characteristics of the user comprises accessing an age, a gender, a weight, and a health-related goal of the user;
wherein identifying the group of users, in the population of users, comprises identifying the group of users, in the population of users, characterized by ages, gender, weights, and health-related goals similar to the age, the gender, the weight, and the health-related goal of the user.

13. The method in claim 1, further comprising:
detecting an exigent circumstance experienced by the user;
generating a recommendation for an off-schedule dosage of a second product associated with a second effect related to the exigent circumstance;
estimating a time to the second effect felt by the user responsive to consumption of the off-schedule dosage of the second product; and
presenting the recommendation and the second time to the second effect felt by the user via a display of the computing device.

14. The method in claim 13:
wherein detecting the exigent circumstance experienced by the user comprises determining that the user has remained awake for a period of time greater than a typical time period for the user; and
wherein generating the recommendation for the off-schedule dosage of a second product comprises generating the recommendation for the off-schedule dosage of the second product associated with the second effect comprising wakefulness.

15. The method of claim 1, further comprising:
detecting a first change in dose amounts of the product consumed by the group of users;
detecting a second change in the expected effect felt by the group of user based on feedback provided by the group of users; and
serving a recommendation to the user, via a display of the computing device, to adjust the dosage amount for the product according to the first change in dose amounts to achieve the second change in the expected effect.

16. A method for monitoring consumption of dietary supplement products, the method comprising:
accessing target wellness-related effect selected by a user;
at a recommendation engine, calculating a dosage amount of a product for the user, the product associated with the target wellness-related effect;
initiating a dosage schedule for the product in the dosage amount for the user;
at a dispenser manager, transmitting a prompt to consume a dose of the product, in the dosage amount, to the user via a computing device based on the dosage schedule;
accessing a confirmation of consumption of the dose of the product entered by the user at the computing device;
at a user interface module, estimating a time to the target wellness-related effect felt by the user based on the confirmation of consumption of the dose of the product by the user; and
in response to the confirmation of consumption of the dose of the product by the user, presenting to the user, via the computing device, the time to the target wellness-related effect felt by the user.

17. The method of claim 16:
further comprising:
accessing a set of characteristics of the user; and
identifying a group of users, in a population of users, exhibiting characteristics similar to the user based on the set of characteristics of the user; and
wherein calculating the dosage amount of the product for the user comprises calculating the dosage amount of the product for the user based on dosage history and feedback for the product from the group of users.

18. The method of claim 17, wherein transmitting the prompt to the user to consume the dose of the product comprises, rendering on a display of the computing device:
the prompt to consume the dose of the product; and
a description of responses to consumption of the product, in the dosage amount, by users in the group of users.

19. The method of claim 16:
wherein estimating the time to the target wellness-related effect felt by the user comprises:
accessing a consumption history of the product by the user;
calculating an adherence to the dosage schedule by the user based on the consumption history; and
estimating a number of days to optimum magnitude of the target wellness-related effect, of the product, felt by the user based on the adherence to the dosage schedule; and
wherein presenting to the user, via the display, the time to the target wellness-related effect felt by the user comprises rendering, on the display, the number of days to optimum magnitude of the target wellness-related effect felt by the user.

20. The method of claim 16:
further comprising:
serving a set of effects to the user via the display;
prompting the user to select an effect from the set of effects; and
identifying the product in response to selection of the target wellness-related effect from the set of effects by the user; and
wherein calculating the dosage amount comprises calculating the dosage amount for the product in response to selection of the target wellness-related effect from the set of effects by the user.

* * * * *